United States Patent [19]

van der Burgt et al.

[11] 4,433,065

[45] Feb. 21, 1984

[54] PROCESS FOR THE PREPARATION OF HYDROCARBONS FROM CARBON-CONTAINING MATERIAL

[75] Inventors: Maarten J. van der Burgt; Sikke J. A. Boelema; Willem J. A. H. Schoeber, all of The Hague; Pieter L. Zuideveld, Amsterdam, all of Netherlands

[73] Assignee: Shell Oil Company, Houston, Tex.

[21] Appl. No.: 355,065

[22] Filed: Mar. 5, 1982

[30] Foreign Application Priority Data

Mar. 24, 1981 [NL] Netherlands ................... 8101447

[51] Int. Cl.³ .............................................. C07C 1/04
[52] U.S. Cl. ................................................... 518/703
[58] Field of Search ............................... 518/702, 703

[56] References Cited

U.S. PATENT DOCUMENTS

| | | | |
|---|---|---|---|
| 2,697,713 | 12/1954 | Gohr et al. | 518/703 |
| 2,713,590 | 7/1955 | Palmer et al. | 518/703 |
| 3,161,461 | 12/1964 | Deal et al. | 23/3 |
| 3,941,820 | 3/1976 | Jackson et al. | 518/703 |
| 4,022,591 | 5/1977 | Staudlinger | 48/76 |
| 4,092,825 | 6/1978 | Egan | 518/703 |
| 4,094,650 | 6/1978 | Koh et al. | 518/702 |
| 4,218,388 | 8/1980 | Schaper et al. | 518/703 |

FOREIGN PATENT DOCUMENTS

| | | | |
|---|---|---|---|
| 152567 | 1/1950 | Australia | 518/703 |
| 957260 | 5/1964 | United Kingdom . | |
| 1436963 | 5/1976 | United Kingdom . | |
| 1501284 | 2/1978 | United Kingdom . | |
| 2006819 | 5/1979 | United Kingdom | 518/728 X |

*Primary Examiner*—Howard T. Mars
*Attorney, Agent, or Firm*—Norris E. Faringer

[57] ABSTRACT

Pulverized coal is converted by means of a gaseous mixture and partial oxidation into synthesis gas which is subsequently utilized as a feedstock for the production of hydrocarbons. A gaseous mixture containing non-converted synthesis gas and low boiling hydrocarbons is separated from the higher boiling hydrocarbons and recycled to the coal conversion step.

8 Claims, 1 Drawing Figure

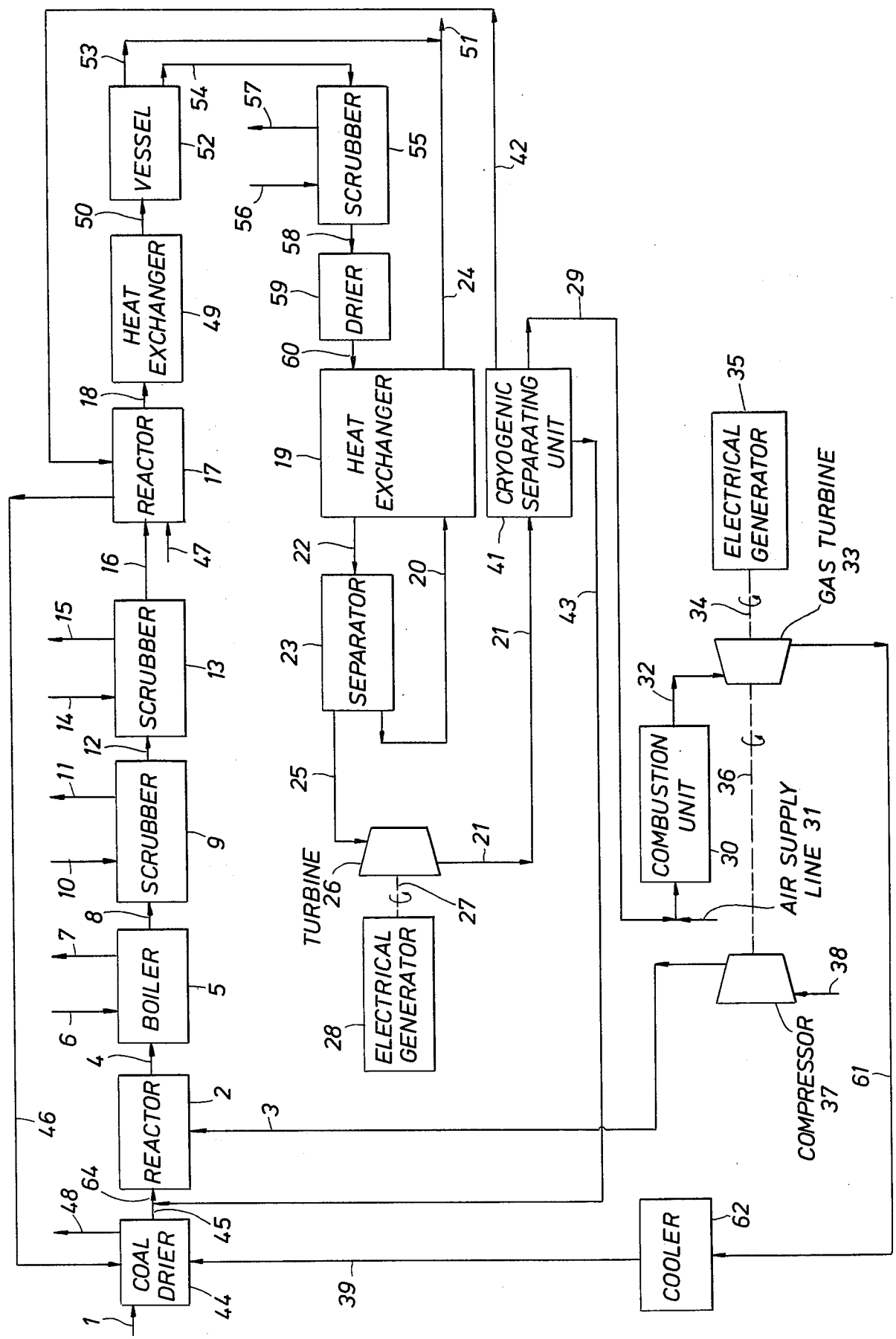

4,433,065

PROCESS FOR THE PREPARATION OF HYDROCARBONS FROM CARBON-CONTAINING MATERIAL

FIELD OF THE INVENTION

The present invention is directed to a process for converting coal by partial oxidation into synthesis gas which is subsequently utilized as a feedstock for the production of hydrocarbons.

BACKGROUND OF THE INVENTION

The partial combustion of carbon-containing material, e.g., coal, to produce synthesis gas, which is essentially carbon monoxide and hydrogen, is well known, and a survey of such known processes is given in "Ullmanns Enzyklopädie der Technischen Chemie", Vol. 10 (1958), pp. 360–458. Several such processes for the preparation of hydrogen and carbon monoxide-containing gases by the partial combustion of coal are currently being utilized world-wide on a commercial scale.

SUMMARY OF THE INVENTION

The present invention relates to a process for the preparation of hydrocarbons from carbon-containing material, characterized in that process comprises the following steps:
(a) the carbon-containing material is converted by gasification into a gas mixture predominantly consisting of carbon monoxide and hydrogen;
(b) the gas mixture obtained in step (a) is partially converted into a hydrocarbon mixture using a catalyst;
(c) the product from step (b) is separated into a gas containing carbon monoxide, hydrogen, methane and ethane, and a final product containing propane and higher boiling hydrocarbons;
(d) at least part of the gas recovered in step (c) is recycled to step (a).

BRIEF DESCRIPTION OF THE DRAWING

The FIGURE illustrates a representative basic flowsheet of the process according to the present invention wherein auxiliary equipment, such as valves, pumps, compressors, instrumentation, etc. have been omitted.

DESCRIPTION OF THE PREFERRED EMBODIMENTS

In the first step of the instant process a mixture of carbon monoxide and hydrogen is prepared by gasification of carbon-containing material, preferably at a temperature between 800° and 2000° C. and more preferably at a temperature between 1050° and 2000° C. As a result of the application of this high temperature, the prepared synthesis gas contains little methane. As compared with a process in which a lower temperature is used in the first step, for example between 800° and 1000° C., the process in which a temperature in excess of 1050° C. is used produces a higher yield of CO and $H_2$ per ton of coal and therefore eventually a higher yield of higher hydrocarbons per ton of carbon-containing material. As a result of the application of a gasification temperature between 1050° and 2000° C. the product also contains only very small amounts of non-gaseous side products, such as tar, phenols and condensable hydrocarbons, if at all present. The absence of these products also results in a higher yield of CO and $H_2$ and consequently in a higher hydrocarbon yield than when a lower temperature is used during the gasification step. In addition, no provisions need be made for the removal of tar, phenols and condensable hydrocarbons from the synthesis gas, which benefits the process economy of gasoline production.

The carbon-containing starting materials in the process according to the invention may be, for example: lignite, bituminous coal, bus-bituminous coal, anthracite, coke, wood and heavy petroleum residues. In order to achieve a more rapid and complete gasification initial pulverization of solid carbon-containing starting material such as coal is preferred. The particle size of this powder is advantageously so selected that 70% of the solid feed can pass a 200-mesh sieve. The gasification is preferably carried out in the presence of oxygen and steam. The purity of the oxygen is preferably at least 90% by volume, nitrogen, carbon dioxide and argon being permissible as impurities. It is preferred to select such a ratio between oxygen and steam that 5–150% by volume of steam is present per part by volume of oxygen. The oxygen used is preferably heated before being contacted with the carbon-containing material. This preheating treatment may very suitably be effected by heat exchange with, for example, the hot product gas prepared according to step (a) of the process. By preheating, the oxygen is preferably brought to a temperature of 200°–500° C.

The reactor in which the gasification is carried out preferably comprises an empty steel vessel which is lined with refractory material and/or cooled on the inside by means of water running through tubes. Suitable reactors are described in the British Pat. No. 1,501,284 and in the U.S. Pat. No. 4,022,591. The high temperature at which the gasification is carried out is obtained by reacting the starting material with oxygen and steam. The mixture to be reacted is preferably passed into the reactor at high velocity. A suitable linear velocity is 10–100 m/sec. The pressure at which the gasification can be effected may vary between wide limits. The absolute pressure is preferably 1–200 bar. In order to convert into gas the largest possible quantity of starting material passed into the reactor, the material should remain in the reactor for some time. It has been found that a residence time of 0.1–12 seconds is sufficient for this purpose. After the starting material has been converted into gas, the reaction product which mainly consists of $H_2$, CO, $CO_2$ and $H_2O$ is removed from the reactor. This gas which normally has a temperature between 1050° and 1800° C. may contain impurities such as ash, carbon-containing solids and hydrogen sulphide. In order to permit removal of the impurities from the gas, the latter should first be cooled. This cooling may very suitably be effected in a boiler in which steam is generated with the aid of waste heat. Although as a rule the solids content of the crude gas leaving the boiler is low, further reduction of the solids content may nevertheless be desirable, for example, if the gas must be desulphurized. To this end the gas is preferably passed through a scrubber where it is washed with water. An apparatus for this purpose has been described in the U.K. Pat. No. 826,209. As a result of such a washing treatment a gas is obtained which contains hardly any solids and has a temperature between 20° and 80° C. The gas may be further purified by removing $H_2S$ and, optionally, at least part of the $CO_2$. The removal of $H_2S$ and $CO_2$ is preferably effected with the aid of the ADIP process or the SULFINOL process, which processes have been described in the U.K. Pat. Nos. 1,444,936, 1,131,989, 965,358, 957,260 and 972,140.

The mixture of carbon monoxide and hydrogen prepared in accordance with the first step of the process according to the invention is converted in the second step into a hydrocarbon mixture using a catalyst. This step may be carried out in any desired manner. If it is desired to obtain an aromatic hydrocarbon mixture, it is to this end preferred to select a catalyst containing a crystalline silicate zeolite of a special type. These zeolites effect a high conversion of aliphatic hydrocarbons into aromatic hydrocarbons in commercially attractive yields and they are in general very active in conversion reactions in which aromatic hydrocarbons are involved.

Zeolites of this type have the following properties:
(a) After dehydration at 400° C. in vacuo they are capable of adsorbing more than 3% by weight of water at 25° C. and saturated water vapor pressure, and
(b) in dehydrated form they have the following overall composition, expressed in moles of the oxides:

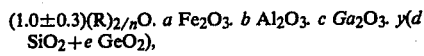
$(1.0\pm0.3)(R)_{2/n}O.\ a\ Fe_2O_3.\ b\ Al_2O_3.\ c\ Ga_2O_3.\ y(d\ SiO_2 + e\ GeO_2),$ wherein
R = one or more mono- or bivalent cations,
$a \geq 0.1$,
$b \geq 0$,
$c \geq 0$,
$a+b+c=1$,
$y \geq 10$,
$d \geq 0.1$,
$e \geq 0$,
$d+e=1$, and
n = the valency of R.

In the process according to the invention it is preferred to use silicates in which no gallium or germanium occur, in other words, silicates for which c and e in the above-mentioned gross composition are 0. In the process according to the invention it is also preferred to use silicates of which a in the above-mentioned gross composition is greater than 0.3 and in particular greater than 0.5. Silicates in which no aluminum occurs, in other words, silicates for which b in the above-mentioned gross composition equals 0, are particularly preferred. It may be noted with regard to y that in the silicates which are used in the process according to the invention, this value is preferably less than 600 and in particular less than 300.

In step (b) of the process according to the invention a mixture of carbon monoxide and hydrogen is advantageously converted into an aromatic hydrocarbon mixture. Step (b) may be carried out per se as a one-stage or two-stage process. In the two-stage process the mixture of carbon monoxide and hydrogen is contacted in the first step with a catalyst containing one or more metal components with catalytic activity for the conversion of an $H_2/CO$ mixture into hydrocarbons and/or oxygen-containing hydrocarbons. In the second step the resultant product is converted into an aromatic hydrocarbon mixture by contacting it under aromatization conditions with the crystalline silicate. In the single-stage process the mixture of carbon monoxide and hydrogen is contacted with a bifunctional catalyst which, in addition to the crystalline silicate, contains one or more metal components with catalytic activity for the conversion of an $H_2/CO$ mixture into hydrocarbons and/or oxygen-containing hydrocarbons. Step (b) of the process according to the invention is preferably carried out as a single-stage process.

In the process according to the invention an $H_2/CO$ mixture is prepared according to step (a), of which the $H_2/CO$ molar ratio may vary within wide limits, depending on the starting material and reaction conditions. Before this mixture is further converted according to step (b), its $H_2/CO$ molar ratio may be changed by addition of hydrogen or carbon monoxide. The hydrogen content of the mixture may also be augmented by applying the known water gas shift reaction to it. It is preferred to use as feed for step (b) of the process according to the invention a gas mixture of which the $H_2/CO$ molar ratio is more than 0.4.

If the mixture of carbon monoxide and hydrogen which is used in the process according to the invention as feed for step (b) has an $H_2/CO$ molar ratio of less than 1.0, step (b) is preferably carried out as a mono-stage process by contacting the gas with a tri-functional catalyst containing one or more metal components with catalytic activity for the conversion of an $H_2/CO$ mixture into hydrocarbons and/or oxygen-containing hydrocarbons, one or more metal components with catalytic activity for the water gas shift reaction and the crystalline silicate. The ratio in which the three catalytic functions are present in the catalyst may vary within wide limits and is mainly determined by the activity of each of the catalytic functions. When a tri-functional catalyst is used in step (b) of the process according to the invention for the conversion of an $H_2/CO$ mixture with an $H_2/CO$ molar ratio of less than 1.0, it is the object that the largest possible quantity of the acyclic hydrocarbons and/or oxygen-containing hydrocarbons which have been formed under the influence of a first catalytic function, is converted under the influence of a second catalytic function into an aromatic hydrocarbon mixture predominantly boiling in the gasoline range, while the largest possible quantity of the water liberated during the conversion of the mixture of carbon monoxide and hydrogen into hydrocarbons and/or during the conversion of the oxygen-containing hydrocarbons into an aromatic hydrocarbon mixture reacts under the influence of a third catalytic function with the quantity of carbon monoxide present in an excess amount in the mixture of carbon monoxide and hydrogen with formation of a mixture of hydrogen and carbon dioxide. Consequently, when an optimum tri-functional catalyst is composed for use in step (b) of the process according to the invention, which catalyst contains a certain quantity of a first catalytic function with a given activity, a lesser quantity of the other catalytic functions may suffice the more active they are.

Although the trifunctional catalysts applicable in step (b) of the process according to the invention are described in this patent application as catalysts containing one or more metal components with catalytic activity for the conversion of an $H_2/CO$ mixture into hydrocarbons and/or oxygen-containing hydrocarbons and one or more metal components with catalytic activity for the water gas shift reaction, this in no way means that separate metal components which each per se possess either catalytic function should invariably be present in the catalysts. It has actually been found that metal components and combinations of metal components having catalytic activity for the conversion of an $H_2/CO$ mixture into predominantly oxygen-containing hydrocarbons as a rule also possess adequate catalytic activity for the water gas shift reaction, so that in that instance it will suffice to incorporate one metal component or one combination of metal components in the catalysts. Examples of such metal components are the metals selected from the group formed by the metals zinc, copper and chromium. When trifunctional catalysts are used in step (b) of the process according to the invention which catalysts contain these metals, preference is accorded to catalysts which contain combinations of at least two of these metals, for example the combination zinc-copper, zinc-chromium or zinc-copper-chromium. Particular preference is given to a trifunctional catalyst which contains the metal combination zinc-chromium in addition to the crystalline silicate. The metal components and combinations of metal components with catalytic activity for the conversion of an $H_2/CO$ mixture into predominantly hydrocarbons do not always possess adequate activity for the water gas shift reaction. When such metal components or combinations of metal components are used in the catalysts, one or more individual metal components with catalytic activity for the water gas shift reaction should therefore be incorporated in the catalysts.

The trifunctional catalysts which are used in step (b) of the process according to the invention are preferably composed of two or three separate catalysts which for convenience's sake will be designated as catalysts X, Y and Z. Catalyst X is the catalyst which contains the metal components with catalytic activity for the conversion of an $H_2/CO$ mixture into the hydrocarbons and/or oxygen-containing hydrocarbons. Catalyst Y is the crystalline silicate. Catalyst Z is the catalyst which contains the metal component with catalytic activity for the water gas shift reaction. As has been explained above, the use of a catalyst Z may in some cases be omitted.

If as catalyst X use is made of a catalyst which is capable of converting an $H_2/CO$ mixture into predominantly oxygen-containing hydrocarbons, a catalyst is preferably selected which is capable of converting the $H_2/CO$ mixture into mainly methanol and/or dimethyl ether. For the conversion of an $H_2/CO$ mixture into mainly methanol, catalysts containing the above-mentioned metal combinations are highly suitable. If desired, the above metal combinations may be supported on a carrier material. By the introduction of an acid function into these catalysts, for example by supporting the metal combination on an acid carrier, it is possible to achieve conversion of the $H_2/CO$ mixture into dimethyl ether, apart from into methanol, to a considerable extent.

Catalysts X which are capable of converting an $H_2/CO$ mixture into predominantly hydrocarbons are known in the literature as Fischer-Tropsch catalysts. Catalysts of this type often contain one or more metals of the iron group or ruthenium together with one or more promoters to augment the activity and/or selectivity and sometimes a carrier material such as kieselguhr. They may be prepared by precipitation, by fusion and by impregnation. The preparation by impregnation of the catalysts which contain one or more metals of the iron group is effected by impregnating a porous carrier with one or more aqueous solutions of salts of metals of the iron group and optionally of promoters, followed by drying and calcining of the composition. If use is made in step (b) of the process according to the invention of a catalyst combination in which catalyst X is a Fischer-Tropsch catalyst, it is preferred to select an iron or cobalt catalyst for this purpose, in particular such a catalyst which has been prepared by impregnation. The relevant catalysts contain, per 100 parts by weight of carrier, 10–75 parts by weight of one or more of the metals of the iron group together with one or more promoters in a quantity of 1–50% of the quantity of the metals of the iron group present on the catalyst, which catalysts have such a specific average pore diameter (p) of at most 10,000 nm and such a specific average particle diameter (d) of at most 5 mm, that the quotient p/d is greater than 2 (p in nm and d in mm).

If it is envisaged in step (b) of the process according to the invention to use a catalyst combination of which X is a Fischer-Tropsch iron catalyst, it is preferred to select an iron catalyst which contains a promoter combination consisting of an alkali metal, a readily reducible metal, such a copper or silver, and optionally a metal which is difficult to reduce, such as aluminum or zinc. A very suitable iron catalyst for the present purpose is a catalyst prepared by impregnation which contains iron, potassium and copper on silica as carrier. If it is envisaged in step (b) of the process according to the invention to use a catalyst combination of which X is a Fischer-Tropsch cobalt catalyst, it is preferred to select a cobalt catalyst which contains a promoter combination consisting of an alkaline earth metal and thorium, uranium or cerium. A very suitable Fischer-Tropsch cobalt catalyst for the present purpose is a catalyst prepared by impregnation which contains cobalt, magnesium and thorium on silica as carrier. Other highly suitable Fischer-Tropsch cobalt catalysts obtained by impregnation are catalysts which, in addition to cobalt, contain one of the elements chromium, titanium, zirconium and zinc on silica as carrier. If desired, it is also possible to use in step (b) of the process according to the invention catalyst combinations which contain a catalyst X capable of converting an $H_2/CO$ mixture into a mixture which contains both hydrocarbons and oxygen-containing hydrocarbons in comparable quantities. As a rule such a catalyst also has adequate catalytic activity for the water gas shift reaction so that the use of a catalyst Z in the combination may be omitted. An example of a catalyst X of this type is an iron chromium oxide catalyst. If desired, it is also possible to use in step (b) of the process according to the invention catalyst combinations which contain two or more catalysts X, for example in addition to a catalyst of the type X which is capable of converting an $H_2/CO$ mixture predominantly into hydrocarbons, a second catalyst of the type X capable of converting an $H_2/CO$ mixture predominantly into oxygen-containing hydrocarbons.

Catalysts Z which are capable of converting an $H_2/CO$ mixture into an $H_2/CO_2$ mixture are known in the literature as CO-shift catalysts. Catalysts of this type often contain one or more metals selected from the group formed by iron, chromium, zinc, copper, cobalt, nickel and molybdenum as catalytically active component, either as such or in the form of their oxides or sulphides. Examples of suitable CO-shift catalysts are the mixed sulphidic catalysts, and the spinel catalysts. If in step (b) of the process according to the invention use is made of a catalyst combination in which catalyst Z occurs, it is preferred to use for this purpose a catalyst containing both copper and zinc, in particular a catalyst in which the Cu/Zn atomic ratio is between 0.25 and 4.0.

In the trifunctional catalysts the catalysts X, Y and optionally Z may be present as a mixture in which each particle of catalyst X is in principle surrounded by a number of particles of catalyst Y and optionally Z and vice versa. When the process is carried out using a fixed catalyst bed, this bed may be composed of alternate layers of particles of the catalysts X, Y and optionally Z. If two or three catalysts are used as a mixture, this mixture may be a macromixture or a micromixture. In the former case the trifunctional catalyst consists of two or three types of macroparticles, one type consisting completely of catalyst X, the second type completely of catalyst Y and optionally the third type completely of catalyst Z. In the latter case the trifunctional catalyst consists of one type of macroparticles, each macroparticle being composed of a large number of microparticles of each of the catalysts X, Y and optionally Z. Trifunctional catalysts in the form of micromixtures may, for example, be prepared by thoroughly mixing a fine powder of catalyst X with a fine powder of catalyst Y and optionally with a fine powder of catalyst Z and shaping the mixture to larger particles, for example by extrusion or molding. In step (b) of the process according to the invention is is preferred to use trifunctional catalysts in the form of micromixtures. The trifunctional catalysts may also be prepared by incorporating the metal components with catalytic activity for the conversion of an $H_2/CO$ mixture into hydrocarbons and/or oxygen-containing hydrocarbons and optionally the metal components with catalytic activity for the water gas shift reaction into the crystalline silicate, for example by impregnation or by ion exchange.

The crystalline silicates which are used in step (b) of the process according to the invention are as a rule prepared by starting with an aqueous mixture containing the following compounds in a certain ratio: one or more compounds of an alkali or alkaline earth metal, one or more compounds which contain a mono- or bivalent organic cation or from which such a cation is formed during the preparation of the silicate, one or more silicon compounds, one or more iron compounds and optionally one or more aluminum, gallium and/or germanium compounds. The preparation takes place by keeping the mixture at elevated temperature until the silicate has been formed and by subsequently separating the silicate crystals from the mother liquor.

The silicates prepared in this way contain alkali and/or alkaline earth metal ions as well as mono- and/or bivalent organic cations. Before they are used in step (b) of the process according to the invention it is preferred to convert at least part of the mono- and/or bivalent organic cations introduced during the preparation into hydrogen ions, for example by calcination, while preferably at least part of the interchangeable mono- and/or bivalent cations introduced during the preparations are substituted by other ions, in particular hydrogen ions, ammonium ions and/or ions of the rare earth metals. The crystalline silicates which are used in step (b) of the process according to the invention preferably have an alkali metal content of less than 1% by weight and in particular of less than 0.05% by weight. If desired, a binder material, such as bentonite or kaolin, may be incorporated in the catalysts used in step (b) of the process according to the invention.

Step (b) of the process according to the invention is preferably carried out at a temperature of 200°–500° C. and in particular of 300°–450° C., a pressure of 1–150 bar and in particular of 5–100 bar, and a space velocity of 50–5000 and in particular 300–3000 Nl of gas/l of catalyst/h.

Step (b) of the process according to the invention may very suitably be carried out by passing the feed in an upward or downward direction through a vertically arranged reactor which contains a fixed or moving bed of the relevant trifunctional catalyst. Step (b) of the process may, for example, be carried out in a fixed-bed operation, in bunker flow operation or in ebullated bed operation. In these processes it is preferred to use catalyst particles having a diameter between 1 and 5 mm. If desired, step (b) of the process can also be carried out in fluidized-bed operation or with the use of a suspension of the catalyst in a hydrocarbon oil. It is then preferred to use catalyst particles having a diameter between 10 and 150 microns.

Sometimes it is desirable to obtain a paraffinic hydrocarbon mixture as final product of the process according to the invention.

Use is then made in step (b) of a Fischer-Tropsch catalyst. Catalysts of this type have been described in detail above. A survey of the known processes for the preparation of aliphatic hydrocarbons by reacting CO with $H_2$ is also given in "Ullmanns Enzyklopädie der technischen Chemie" (1957), Vol. 9, pp. 684–748. These hydrocarbon synthesis are preferably carried out at a temperature in the range of 200°–300° C. and a pressure between 10 and 30 atm. abs., while it is advantageous to use iron, cobalt, nickel or ruthenium-containing catalysts.

Since the hydrocarbon synthesis is highly exothermic, the interior of the reactor used is often cooled. Cooling is advantageously effected with water which is converted into steam. At least part of this steam is suitably used to dry at least part of the carbon-containing starting material.

This is done in a manner known per se, such as for example described in "Chemical Engineers' Handbook" by R. H. Perry and C. H. Chilton (1973), pp. 20-4 to 20-63. Drying is preferably carried out in a rotating drier in which the starting material is dried with condensing steam by indirect heat exchange.

The product of the hydrocarbon synthesis step (b) is subsequently separated in step (c) into a liquid, containing hydrocarbons with at least 3 carbon atoms and a gas containing unconverted hydrogen, carbon monoxide, nitrogen and resultant hydrocarbons with at least 2 carbon atoms. To this end the product of step (b) is preferably cooled at a pressure between 20–100 atm. abs. to a temperature between 0° and −70° C. Water and carbon dioxide are removed before the temperature decreases below the respective freezing points. The liquid is heated to a temperature between 0° and 40° C., preferably by heat exchange with the product from the hydrocarbon synthesis, and subsequently removed from the system as final product. Depending on the catalyst(s) used this final product substantially consists of normal paraffins having a number of carbon atoms ranging from 3 to 50 and/or of aromatics having a number of carbon atoms ranging from 6 to 12. The gas is preferably expanded in a back pressure turbine to a pressure ranging from 3 to 20 atm. abs., so that the gas cools down to a temperature between −50° and −70° C. With the aid of this back pressure turbine, energy is advantageously generated which may be used in the system, for example for driving pumps and compressors.

At least part of the expanded cooled gas is then preferably used to cool the product of step (b) by indirect heat exchange, during which operation it assumes a temperature ranging from −25° to −5° C. It is then advantageous to completely combust this warmed-up gas with air or with oxygen-enriched air and the hot combustion gases are utilized in a gas turbine known per se which generated energy which is at least partly used for the compression of the oxygen, the air or the oxygen-enriched air for step (a) and for the complete combustion of the gas. The gas turbine off-gases are at least in part used in a suitable manner to dry the coal. Conventional gas turbines for this purpose are described in "Chemical Engineers' Handbook" by R. H. Perry and C. H. Chilton (1973), pp. 24-28 to 24-36.

Another suitable possibility for utilizing the $C_2$ hydrocarbons containing gas resides in that at least part of it is recycled to step (a) wherein the hydrocarbon components are converted by partial combustion, mainly into CO and $H_2$. During this recirculation it is advantageous to transport pulverulent coal with the aid of this gas to the gasifying reactor of step (a).

According to a highly preferred embodiment of the process according to the invention at least part of the gas expanded in the back-pressure turbine, which gas has a temperature between −50° and −70° C., is separated cryogenically into a gas substantially consisting of hydrogen, a gas substantially consisting of carbon monoxide, nitrogen and argon and into a gas substantially consisting of methane and ethane. At least part of the gas predominantly consisting of hydrogen is advantageously recycled to step (b).

At least part of the gas substantially consisting of carbon monoxide, nitrogen and argon is advantageously combusted with air, optionally enriched with oxygen, and the thermal energy of the hot combustion off-gas is advantageously converted in a gas turbine into mechanical energy. During this operation a hot gas is liberated, optionally after further cooling, which gas has a temperature between 200° and 300° C. which is eminently suitable for drying the coal.

At least part of the gas substantially consisting of methane and ethane is preferably recycled to step (a) where these hydrocarbons are converted into synthesis gas.

It may then be used to transport the starting material in powder form to step (a). This pneumatic transport is effected in a manner known per se, as is, for example, described in "Chemical Engineers' Handbook", by R. H. Perry and C. H. Chilton (1973), pp. 7-16 to 7-21.

The advantage of the process according to the invention over the conventional processes in which the above-mentioned recirculations are not applied, resides in a higher yield propane and higher-boiling hydrocarbons per unit weight of converted coal.

The invention will now be described with particular reference to the attached FIGURE showing a basic lay-out of the process according to the invention, to which; however, the invention is by no means limited. Auxiliary equipment, such as valves, pumps and compressors, have been omitted from this FIGURE.

Pulverulent coal is passed via a line 1 into a coal drier 44 where the coal is dried, directly with the aid of flue gas having a temperature of 250° C. supplied through a line 39 and/or indirectly with the aid of steam having a temperature of 220° C. supplied through a line 46 and discharged through a line 48; the dry coal is subsequently discharged through a line 45 and passed through a line 64 into a gasifying reactor 2 with the aid of at least part of a gas containing methane and ethane which is supplied through a line 43. In the reactor the coal is gasified at a temperature of 1500° C. and a pressure of 35 atm. abs. with oxygen which is supplied through a line 3. The gasification product is passed to a boiler 5 through a line 4 in which boiler the product is cooled down to a temperature of 160° C. In the boiler 5, water which is supplied through a line 6 is converted into steam which is discharged through a line 7. The cooled gasification product is passed through a line 8 to a scrubber 9 in which the product is freed from ash and soot. Clean water is supplied to the scrubber 9 via a line 10 while soot and ash-containing water is discharged through a line 11. The soot and ash-freed gas is passed through a line 12 to a scrubber 13 in which the gas is purified from $H_2S$, COS and $CO_2$ with the aid of a solution of di-isopropanolamine and sulfolane in water. The fresh solution is supplied through line 14. The laden solution is discharged through line 15. During washing the purified gas is further cooled down to 40° C. It is passed to a hydrocarbon synthesis reactor 17 through a line 16 in which reactor part of the CO and $H_2$ present in the gas interreacts to form hydrocarbons.

In the reactor 17 use is made of a catalyst 47 containing cobalt, which is supported on a silica carrier.

The hydrocarbon synthesis is carried out at a temperature of 250° C. and a pressure of 30 atm. abs. The hydrocarbon synthesis product is discharged through a line 18 to a heat exchanger 49 where it is cooled to 40° C. The cooled product is passed to vessel 52 through line 50, in which vessel a liquid separates which is discharged through line 53 and a gas which proceeds to scrubber 55 through line 54, where $CO_2$ is removed with the aid of a solution of di-isopropanolamine and sulfolane in water. The fresh solution is supplied through line 56 and the laden solution is discharged through line 57.

The purified gas is passed through a line 58 to drier 59 where it is freed from water. The gas is passed through line 60 to a heat exchanger 19 in which it is cooled to −20° C. by heat exchange with a cold stream 20. The cooled hydrocarbon synthesis product is passed through a line 22 to a separator 23 where it is separated into a liquid consisting of hydrocarbons having at least 3 carbon atoms and a gas containing unconverted $H_2$ and CO and $N_2$ and hydrocarbons having not more than 2 carbon atoms. The liquid is passed to the heat exchanger 19 through the line 20 and subsequently combined by means of line 24 with the liquid supplied through the line 53. The combined liquid flow is discharged as final product through a line 51. The gas is passed through a line 25 to a back-pressure turbine 26 in which it is expanded to 15 atm. abs. while being cooled down to −60° C. The turbine 26 is connected to a generator 28 by means of a shaft 27, in which generator electrical energy is generated. The expanded cold gas is passed to a cryogenic separating unit 41 through a line 21. In this unit the gas is separated into a hydrogen-rich gas which is passed to the hydrocarbon synthesis reactor 17 through a line 42, a CO, $N_2$ and argon-containing gas and a gas substantially consisting of methane and ethane. The CO, $N_2$ and argon-containing gas leaves the cryogenic separating unit 41 through a line 29 wherein it is passed to the combustion unit 30. In this unit the gas is combusted with air supplied through a line 31. The hot combustion gases from the combustion unit 30 have a temperature of 1100° C. and are passed to a gas turbine 33 through a line 32. In this turbine the thermal energy is converted to mechanical energy which is used on the one hand to drive an electrical generator 35 by means of shaft 34 and, on the other hand, to drive a compressor 37 by means of shaft 36, in which compressor oxygen is compressed which is supplied through a line 38 and which is passed to the gasifier 2 through a line 3. The flue gas used in gas turbine 33 is passed through line 61 to cooler 62 in which it is cooled to a temperature of 250° C. and it is discharged through a line 39 at a pressure of 1 atm. abs. to the coal drier 44.

The gas substantially consisting of methane and ethane is passed through the lines 43 and 64 to the gasifying reactor 2 where it is converted, together with the coal which the gas has taken up in line 64, into a gas substantially consisting of $H_2$ and CO.

The invention will now be further elucidated with reference to the following Example.

EXAMPLE

The starting material used was coal having the following composition:

|     | % by weight |
| --- | --- |
| C   | 58.6 |
| H   | 4.2 |
| O   | 8.6 |
| S   | 3.5 |
| N   | 1.1 |
| ash | 7.6 |

This coal contained 35% by weight of volatile components and also 7.6% by weight of water.

A throughput of 10,000 tons/day of the coal was first dried, directly with 5400 t/d of hot off-gas (temperature 250° C.) from a gas turbine and indirectly in a rotating drier with 2400 tons/day of steam (temperature 210° C.) which had been generated, and was then gasified during the subsequent hydrocarbon synthesis by partial combustion with the aid of 0.9 kg of $O_2$ per kg of water- and ash-free coal in a plant as diagrammatically shown in the FIGURE. The temperature was 1500° C. and the pressure 35 atm. abs.

After cooling down to 40° C. and removal of the solid matter the resultant gas (1400 tons/day) had the following composition:

|       | % by volume |
| ----- | ----------- |
| $H_2O$ | 0.2 |
| $H_2$  | 30.4 |
| CO    | 65.0 |
| $CO_2$ | 2.0 |
| $CH_4$ | 0.02 |
| $H_2S$ | 1.4 |
| COS   | 0.2 |
| $N_2$ + A | 0.8 |

This gas was purified with the aid of the Sulfinol process in which process the gas was washed at 40° C. and 31 atm. abs. with a mixture of sulfolane, di-isopropanolamine and water.

The composition of the purified gas was as follows:

|       | % by volume |
| ----- | ----------- |
| $H_2O$ | 0.2 |
| $H_2$  | 31.5 |
| CO    | 67.4 |
| $CH_4$ | 0.02 |
| $N_2$ + A | 0.8 |

This gas was heated to 250° C. and it was passed at this temperature and a pressure of 30 atm. abs. over a catalyst to form hydrocarbons. The catalyst had the following composition:

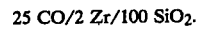

25 CO/2 Zr/100 $SiO_2$.

The product of the hydrocarbon synthesis (3750 tons/day) was separated into a liquid fraction (2530 tons/day) consisting of hydrocarbons having at least 3 carbon atoms and a gas (1220 tons/day) which contained $H_2$, CO, $N_2$, argon and hydrocarbons having at most 2 carbon atoms.

The separation and the subsequent heat exchanges took place as mentioned in the description of the FIGURE.

The gas was first expanded in a back-pressure turbine, while cooling to $-60°$ C., after which it was separated into a hydrogen-rich gas (90 tons/day), a CO, $N_2$ and argon-containing gas (750 tons/day) and a gas mainly consisting of methane and ethane (380 tons/day). The CO, $N_2$ and argon-containing gas was completely combusted. The hot combustion gases (5400 tons/day), temperature (1100° C.) were passed through a gas turbine and subsequently used to dry the coal. Both the back-pressure turbine and the gas turbine were coupled to electrical power generators.

The compressor for the combustion air for the partial and complete combustion was driven by the gas turbine.

The gas substantially consisting of methane and ethane was recycled to the partial coal combustion stage and converted there into CO and $H_2$.

By means of the above-described process 334 kg of hydrocarbons having at least 3 carbon atoms were produced from 1000 kg of water and ash-free coal, while 105 kWh of electrical energy were generated.

What is claimed is:

1. A process for the preparation of hydrocarbons from coal comprising the following steps:
(a) a finely comminuted coal is converted by gasification at a temperature from 1050° to 2000° C. in the presence of oxygen and steam into a gas mixture consisting substantially of carbon monoxide and hydrogen;
(b) the gas mixture obtained in step (a) is partially converted into a aromatic hydrocarbon mixture with the use of a bifunctional crystalline silicate catalyst which
(i) is capable of adsorbing more than 3% by weight of water at 25° C. and saturated water vapor pressure after dehydration at 400° C. in vacuo, and
(ii) has, in the dehydrated form, the following gross composition, expressed in moles of the oxides:

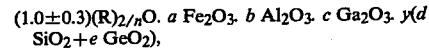

$(1.0 \pm 0.3)(R)_{2/n}O . a\ Fe_2O_3 . b\ Al_2O_3 . c\ Ga_2O_3 . y(d\ SiO_2 + e\ GeO_2)$, wherein
R = one or more mono- or bivalent cations,
$a \geq 0.1$,
$b \geq 0$,
$c \geq 0$,
$a + b + c = 1$, $y \geq 10$,
$d \geq 0.1$,
$e \geq 0$,
$d + e = 1$, and
n = the valency of R, and (iii) which contains one or more metal components with catalytic activity for conversion of an H₂/CO mixture into hydrocarbons and/or oxygen-containing hydrocarbons;

(c) the product of step (b) is separated into a liquid containing hydrocarbon with at least 3 carbon atoms and a gas containing unconverted hydrogen, carbon monoxide, nitrogen and resultant hydrocarbon gases; and (d) at least a part of the gas product of step (c) is separated into (i) a gas consisting substantially of hydrogen, (ii) a gas consisting substantially of carbon monoxide, nitrogen and argon, and (iii) a gas consisting substantially of methane and ethane and wherein at least a part of gas (i) is recycled to step (b) and at least a part of gas (iii) is recycled to step (a).

2. The process of claim 1 wherein at least part of the gas recovered in step (c) is combusted in a gas turbine to form a hot combustion gas during which process energy is generated.

3. The process of claim 2 wherein at least part of the finely comminuted coal is dried by at least part of the hot combustion gas.

4. The process of claim 1 wherein the reaction mixture is indirectly cooled in step (b) with the aid of water which is converted into steam and at least part of this steam is used to indirectly dry at least part of the carbon-containing material.

5. The process of claim 1 wherein at least part of the gas substantially consisting of carbon monoxide, nitrogen and argon is combusted in a gas turbine during which operation energy is generated.

6. The process of claim 1 wherein a mixture of finely comminuted coal, oxygen and steam is passed into a gasification reactor at a linear velocity of 10–100 m/sec.

7. The process of claim 1 wherein step (b) is carried out at a temperature of 200°–500° C., a pressure of 1–150 bar and a space velocity of 50–5000 Nl of gas/l of catalyst/hour.

8. The process of claim 1 wherein the separation of step (c) is carried out at a pressure ranging from 20 to 100 bar absolute and a temperature ranging from 0° to −70° C.

* * * * *